(12) United States Patent
Guo et al.

(10) Patent No.: US 11,992,322 B2
(45) Date of Patent: May 28, 2024

(54) HEART RHYTHM DETECTION METHOD AND SYSTEM USING RADAR SENSOR

(71) Applicant: ioNetworks INC., New Taipei (TW)

(72) Inventors: Jing-Ming Guo, New Taipei (TW); Ting Lin, New Taipei (TW); Chia-Fen Chang, New Taipei (TW); Jeffry Susanto, New Taipei (TW); Yi-Hsiang Lin, New Taipei (TW); Po-Cheng Huang, New Taipei (TW); Yu-Wen Wei, New Taipei (TW)

(73) Assignee: IONETWORKS INC., New Taipei (TW)

( * ) Notice: Subject to any disclaimer, the term of this patent is extended or adjusted under 35 U.S.C. 154(b) by 319 days.

(21) Appl. No.: 17/218,142

(22) Filed: Mar. 30, 2021

(65) Prior Publication Data

US 2022/0313138 A1    Oct. 6, 2022

(51) Int. Cl.
*A61B 5/346* (2021.01)
*A61B 5/00* (2006.01)
*A61B 5/333* (2021.01)

(52) U.S. Cl.
CPC ............. *A61B 5/346* (2021.01); *A61B 5/333* (2021.01); *A61B 5/7203* (2013.01); *A61B 5/7257* (2013.01); *A61B 5/7264* (2013.01)

(58) Field of Classification Search
CPC ....... A61B 5/346; A61B 5/333; A61B 5/7203; A61B 5/7257; A61B 5/7264; A61B 5/0507; A61B 5/7225; A61B 5/7267; G01S 7/415; G01S 7/417; G01S 13/34; G01S 13/583; G01S 13/88; G06N 3/02; G06N 3/0464
See application file for complete search history.

(56) References Cited

U.S. PATENT DOCUMENTS

| | | | | |
|---|---|---|---|---|
| 8,086,304 | B2 * | 12/2011 | Brockway | G16H 50/20 600/515 |
| 11,829,959 | B1 * | 11/2023 | Latif | G06V 20/182 |
| 2009/0043216 | A1 * | 2/2009 | Lin | A61B 5/7214 600/407 |
| 2018/0338732 | A1 * | 11/2018 | Chiao | A61B 5/681 |
| 2019/0130257 | A1 * | 5/2019 | Meyerson | G06N 3/045 |
| 2020/0085382 | A1 * | 3/2020 | Taerum | G06T 7/0016 |
| 2020/0265276 | A1 * | 8/2020 | Xu | A61B 5/7264 |

(Continued)

OTHER PUBLICATIONS

He, T., et al. (2019). Bag of tricks for image classification with convolutional neural networks. In Proceedings of the IEEE/CVF conference on computer vision and pattern recognition (pp. 558-567) (hereinafter, "He") (Year: 2019).*

(Continued)

*Primary Examiner* — Oommen Jacob
(74) *Attorney, Agent, or Firm* — Chun-Ming Shih; LANWAY IPR SERVICES

(57) ABSTRACT

A heart rhythm detection method and system by using radar sensor is capable of collecting an original signal using a radar sensor toward at least one subject, and converting the original signal to a two dimensional image information (i.e., spectrogram) using the concept of image vision. Then, the neural network automatically learns which heartbeat frequency should be focused on and which heartbeat frequency should be filtered out in the two dimensional image information through deep learning, so that the heartbeat frequencies can be extracted effectively.

6 Claims, 17 Drawing Sheets

(56) References Cited

U.S. PATENT DOCUMENTS

| | | | | |
|---|---|---|---|---|
| 2021/0004641 | A1* | 1/2021 | Teichner | G06F 18/2431 |
| 2021/0169442 | A1* | 6/2021 | Agarwal | A61B 5/7264 |
| 2021/0325509 | A1* | 10/2021 | Santra | G01S 13/88 |
| 2022/0313138 | A1* | 10/2022 | Guo | A61B 5/7264 |
| 2022/0343638 | A1* | 10/2022 | Wang | G16H 30/40 |

OTHER PUBLICATIONS

Rial [Technological contributions to imaging radars in the millimeter-wave band, Dialnet 2019]. (Year: 2019).*

Xie [Feature Enrichment Based Convolutional Neural Network for Heartbeat Classification From Electrocardiogram, IEEE Access] (Year: 2019).*

Dong [Cardiogram Detection with a Millimeter-wave Radar Sensor, 2020 IEEE Radio and Wireless Symposium (RWS)]. (Year: 2020).*

* cited by examiner

HEART RHYTHM DETECTION METHOD AND SYSTEM USING RADAR SENSOR

BACKGROUND OF THE INVENTION

1. Field of the Invention

The present invention generally relates to a heart rhythm detection method and system using radar sensor; in particular, it relates to a heart rhythm detection method and system using radar sensor capable of applying the feature of automatically finding characteristics through the deep learning, and then allowing the neural network to find the relationship between the heartbeat frequency and other non-heartbeat frequency in the two dimensional image information, and finally detecting the heart rhythm.

2. Description of Related Art

The advent of the Artificial Intelligence (AI) era is changing the structures of human societies, directly or indirectly affecting our daily lives. We all hope that AI can successfully solve problems and improve the quality of life. The combination of AI and medical treatments has been a hot topic all the time, and it is quite common with regard to the applications in terms of disease determination and prediction as well. Due to the complexity of medical signals and the required accuracy, the use of traditional algorithmic processing methods typically has many limitations; accordingly, by using of objective data derived from big data operations, in combination with deep learning, it is possible to enable computers to learn quickly thereby further predicting, judging, classifying and making decisions, such that we can integrate professional diagnoses originally determined by physicians who have been trained for a long time in the hospital into our daily lives via various smart wearable equipments and home-use measuring instruments in order to improve our quality of life and achieve the effect of early prevention. In this way, it can not only solve the dilemma of insufficient medical human resources, but make it possible for AI to surpass human judgment with the advancement of measuring instruments.

Currently, many types of radars already enable the application of radar-based non-contact Vital Signs detections, e.g., UWB, CW Doppler Radar and FMCW; however, it should be noticed that although all such methods can detect normally in a controlled environment and under certain conditions, it is still necessary to solve the uncertainty issues brought by the actual environment in order to make the radar have sufficient capability to detect signs of life in various fields, while such uncertainty issues may include unknown body conditions, sensor shaking and deployment, effective elimination of respiratory harmonics and cluttered surrounding interferences or the like, and negatively affect reliable detection processes. Therefore, in order to solve these uncertainties, it is common to add more signal processes and analyses, more radar devices or alternatively the combination of radar and other sensors.

Consequently, to obtain more reliable measurements and motion compensation, the present invention provides a deep learning algorithm which adopts the Short-Time Fourier Transform (STFT) operation to convert the signal to two dimensional image information (i.e., spectrogram), applying the advantage of deep learning with respect to automatically finding the desired features, then using the network to find the relationship between the heartbeat frequency in the spectrogram and other non-heartbeat frequencies, and finally detecting the heart rhythm, which can successfully solve the aforementioned uncertainty issues so that the present invention may be an optimal solution.

SUMMARY OF THE INVENTION

The present invention discloses a heart rhythm detection method using radar sensor, comprising the following steps:
(1) collecting a raw signal by aligning at least one radar sensor toward at least one subject; and
(2) converting the collected raw signal to two dimensional image information, then learning from the obtained two dimensional image information and automatically filtering out the noise signal by means of the neural network model so as to learn the relationship between the heartbeat frequency and non-heartbeat frequency of the two dimensional image information thereby extracting the heartbeat frequency.

More specifically, the radar sensor is the millimeter wave radar.

More specifically, the raw signal can be first filtering processed then further converted to the two dimensional image information by means of the Fourier Transform.

More specifically, the filtering process can be applied to keep the raw signal within the frequency domain of heart rhythm by means of the high-pass filtering and/or band-pass filtering process.

More specifically, the neural network model applies AvgPooling to improve Res_block.

More specifically, it is required to first detect and determine whether the subject has left thereby maintaining the correctness of signal sampling.

The present invention discloses a heart rhythm detection system using radar sensor, comprising: at least one radar sensor, used for collecting a raw signal by aligning at least one radar sensor toward at least one subject; and at least one server equipment, used for connecting to the radar sensor and capable of receiving the raw signal thus converting the collected raw signal to two dimensional image information, then learning from the obtained two dimensional image information and automatically filtering out the noise signal by means of the neural network model so as to learn the relationship between the heartbeat frequency and non-heartbeat frequency of the two dimensional image information thereby automatically extracting the heartbeat frequency.

More specifically, the server equipment comprises at least one processor and at least one computer readable recording media, and the computer readable recording media stores at least one application program and further stores computer readable instructions such that, upon running the stored computer readable instructions by the processor, the application program can be executed thus converting the raw signal to two dimensional image information, then learning from the obtained two dimensional image information and automatically filtering out the noise signal by means of the neural network model so as to learn the relationship between the heartbeat frequency and non-heartbeat frequency of the two dimensional image information thereby automatically extracting the heartbeat frequency.

More specifically, the application program includes: an input module, used for inputting at least one data file including the raw signal; a filtering process module, connected to the input module in order to filter the raw signal; a two dimensional image conversion module, connected to the filtering process module thereby performing the Fourier Transform in order to convert the signal to the two dimensional image information; and a neural network learning module, connected to the two dimensional image conversion module thereby inputting the two dimensional image information into the neural network learning module which applies AvgPooling to improve Res_block to acquire a neural network model thus learning from the two dimensional image information in the neural network model and automatically filtering out noise signals so as to learn the relationship between the heartbeat frequency and non-heartbeat frequency of the two dimensional image information thereby extracting the heartbeat frequency.

More specifically, the filtering process module can be applied to keep the raw signal within the frequency domain of heart rhythm by means of the high-pass filtering and/or band-pass filtering process.

BRIEF DESCRIPTION OF THE DRAWINGS

FIG. 6A-1 shows a raw signal waveform diagram for the raw signal, without being processed by the filter, of the heart rhythm detection method and system using radar sensor in accordance with the present invention.

FIG. 6A-2 shows a Fourier Transform waveform diagram for the raw signal, without being processed by the filter, of the heart rhythm detection method and system using radar sensor in accordance with the present invention.

FIG. 6A-3 shows a transformed time-frequency spectrum diagram for the raw signal, without being processed by the filter, of the heart rhythm detection method and system using radar sensor in accordance with the present invention.

FIG. 6B-1 shows a raw signal waveform diagram for the raw signal, after being processed with a high-pass filter, of the heart rhythm detection method and system using radar sensor in accordance with the present invention.

FIG. 6B-2 shows a Fourier Transform waveform diagram for the raw signal, after being processed with a high-pass filter, of the heart rhythm detection method and system using radar sensor in accordance with the present invention.

FIG. 6B-3 shows a transformed time-frequency spectrum diagram for the raw signal, after being processed with a high-pass filter, of the heart rhythm detection method and system using radar sensor in accordance with the present invention.

FIG. 6C-1 shows a raw signal waveform diagram for the raw signal, after being processed with a band-pass filter, of the heart rhythm detection method and system using radar sensor in accordance with the present invention.

FIG. 6C-2 shows a Fourier Transform waveform diagram for the raw signal, after being processed with a band-pass filter, of the heart rhythm detection method and system using radar sensor in accordance with the present invention.

FIG. 6C-3 shows a transformed time-frequency spectrum diagram for the raw signal, after being processed with a band-pass filter, of the heart rhythm detection method and system using radar sensor in accordance with the present invention.

DETAILED DESCRIPTION OF THE PREFERRED EMBODIMENTS

Other technical contents, aspects and effects in relation to the present invention can be clearly appreciated through the detailed descriptions concerning the preferred embodiments of the present invention in conjunction with the appended drawings.

Figure 1:
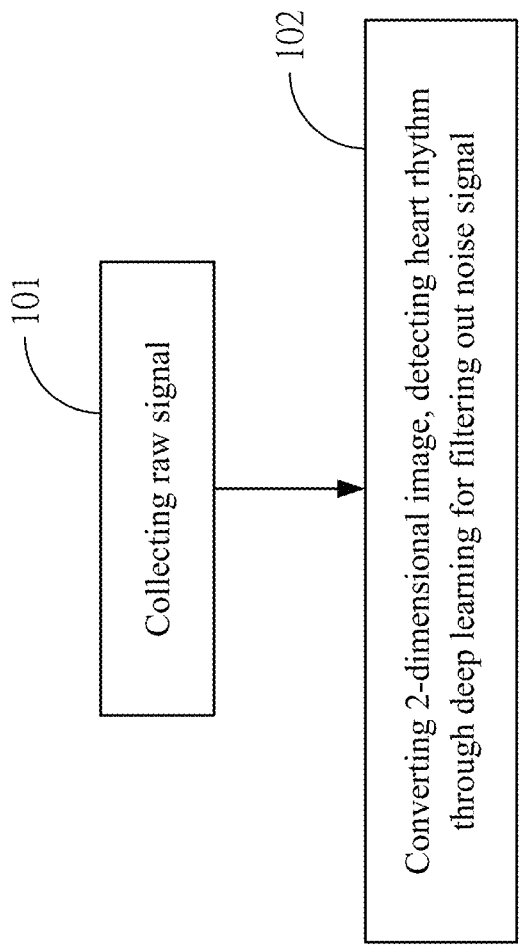
FIG. 1 shows a flowchart for the heart rhythm detection method and system using radar sensor in accordance with the present invention.

Refer initially to FIG. 1, wherein a flowchart for the heart rhythm detection method and system using radar sensor in accordance with the present invention is shown, comprising the follow steps:

(1) collecting a raw signal by aligning at least one radar sensor toward at least one subject (101); and (2) converting the collected raw signal to two dimensional image information, then learning from the obtained two dimensional image information and automatically filtering out the noise signal by means of the neural network model so as to learn the relationship between the heartbeat frequency and non-heartbeat frequency of the two dimensional image information thereby extracting the heartbeat frequency (102).

Figure 2:
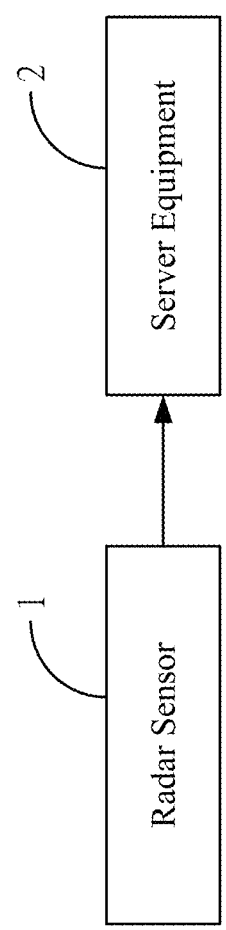
FIG. 2 shows a system architecture view for the heart rhythm detection method and system using radar sensor in accordance with the present invention.
Figure 3:
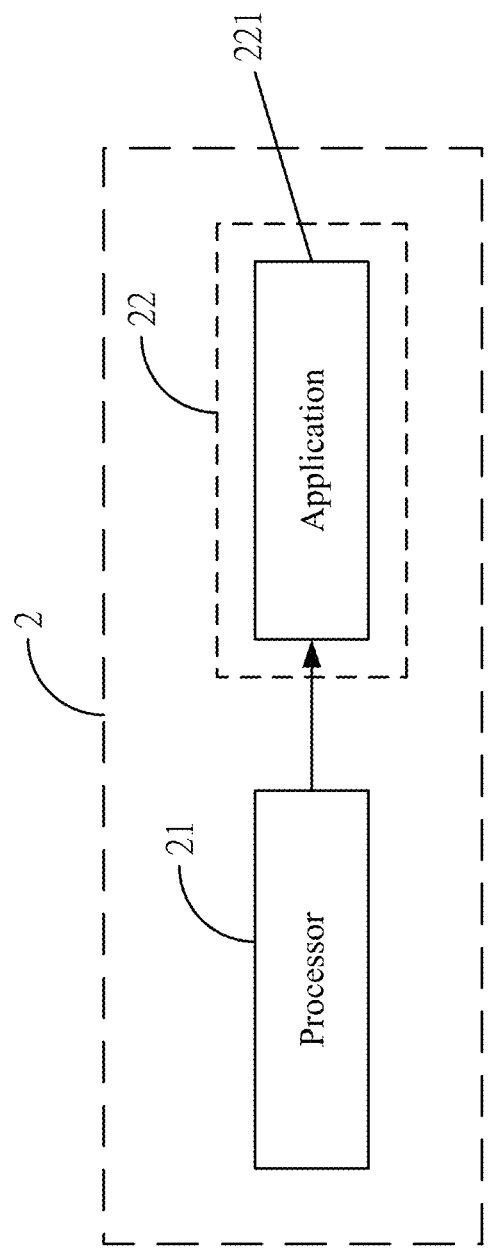
FIG. 3 shows a view for the server equipment in the heart rhythm detection method and system using radar sensor in accordance with the present invention.
Figure 4:
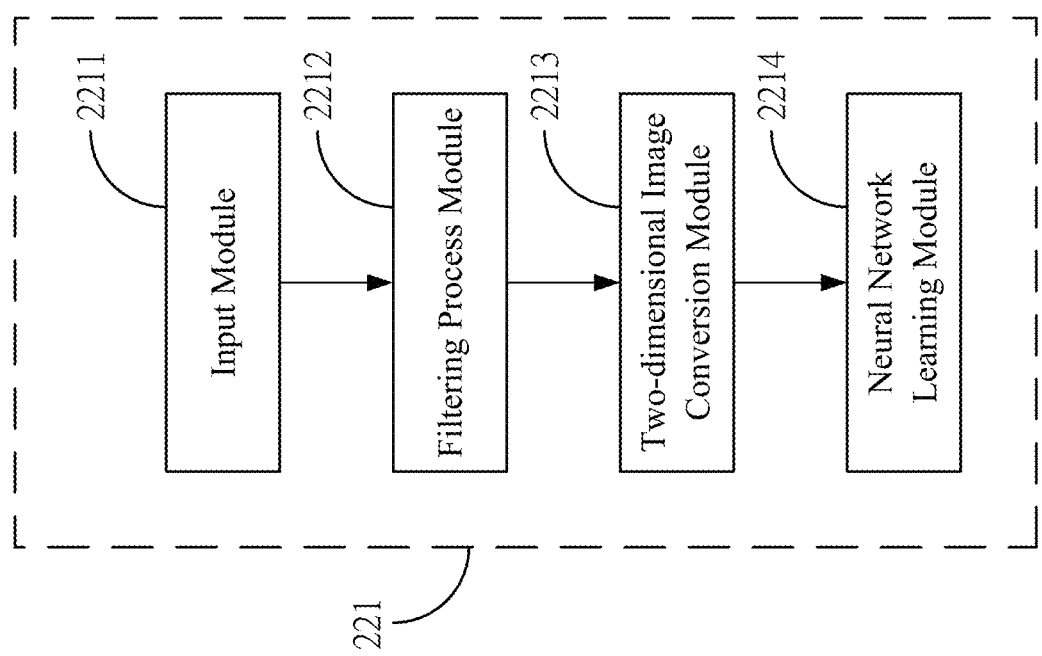
FIG. 4 shows an architecture view for the application program in the heart rhythm detection method and system using radar sensor in accordance with the present invention.

Additionally, as shown in FIGS. 2~4, the heart rhythm detection system using radar sensor according to the present invention comprises:

(1) at least one radar sensor 1, used for collecting a raw signal by aligning at least one radar sensor toward at least one subject, in which the radar sensor is a one-millimeter wave radar;

(2) at least one server equipment 2, used for connecting to the radar sensor 1 and capable of receiving the raw signal thus converting the collected raw signal to two dimensional image information, then learning from the obtained two dimensional image information and automatically filtering out the noise signal by means of the neural network model so as to learn the relationship between the heartbeat frequency and non-heartbeat frequency of the two dimensional image information thereby automatically extracting the heartbeat frequency.

In addition, the server equipment 2 comprises at least one processor 21 and at least one computer readable recording media 22, and the computer readable recording media 22 stores at least one application program 221 and further stores computer readable instructions such that, upon running the stored computer readable instructions by the processor 21, the application program 221 can be executed thus converting the raw signal to two dimensional image information, then learning from the obtained two dimensional image information and automatically filtering out the noise signal by means of the neural network model so as to learn the relationship between the heartbeat frequency and non-heartbeat frequency of the two dimensional image information thereby automatically extracting the heartbeat frequency.

Herein the application program 221 includes:
(1) an input module 2211, used for inputting at least one data file including the raw signal;
(2) a filtering process module 2212, connected to the input module 2211 in order to filter the raw signal, in which the filtering process can be applied to keep the raw signal within the frequency domain of heart rhythm by means of the high-pass filtering and/or band-pass filtering process;
(3) a two dimensional image conversion module 2213, connected to the filtering process module 2212 thereby performing the Fourier Transform in order to convert the signal to the two dimensional image information; and
(4) a neural network learning module 2214, connected to the two dimensional image conversion module 2213 thereby inputting the two dimensional image information into the neural network learning module which applies AvgPooling to improve Res_block to acquire a neural network model thus learning from the two dimensional image information in the neural network model and automatically filtering out noise signals so as to learn the relationship between the heartbeat frequency and non-heartbeat frequency of the two dimensional image information thereby extracting the heartbeat frequency.

Since the raw signal is the original, unprocessed signal, in order to improve the quality of the input signal, after apply the fast Fourier transform (FFT) thereon, it can be found that this signal includes a significant noise signal near 0 Hz; therefore, we designed the following two steps, as described below:
(1) High-Pass Filter, thereby filtering out this significant noise signal, which aims to preserve the frequency domain part of the human heart rhythm before 0.8 Hz; and
(2) Band-Pass Filter, because the heartbeat frequency typically is 50-120 beats per minute, which can be converted to a frequency range of 0.8 Hz-2 Hz, the BPF is applied to lock the entire raw signal in the frequency domain of 0.8~2.0 Hz human heart rhythm; consequently, by using this step, it is possible to limit the signal to this frequency so as to estimate the heart rhythm.

Moreover, the present invention can utilize the Short-Time Fourier Transform (STFT) operation to convert the signal to Time-Frequency dimension thereby transforming the 1D signal to a time-frequency view of 2D image, which is described in details as below:
(1) The so-called "Short-Time Fourier Transform" is a sequential Fourier transform after adding the window signal, which can be applied to determine the sine frequency and phase at the local portion of the signal changing along with time, and the biggest difference thereof from the Fourier transform is that the Fourier transform does not give any information about the changes of the signal frequency with respect to time.
(2) In brief, for the case of continuous time, this window function shifts along the time axis, and the obtained series of Fourier transform results will be arranged into a two-dimensional representation. Mathematically, such operations can be written as:

$$X(t, f) = \int_{-\infty}^{\infty} w(t-\tau)x(\tau)e^{-j2\pi f\tau}d\tau$$

wherein w(t) is the window function, and x(t) is the signal to be transformed. X(t, w) is the Fourier transform of w(t−τ)x(τ), which varies along time t, so that window functions shifts along the time axis. The reason that the present invention chose the STFT operation is to first transform the raw signal then reverse transform back to the original signal, whose loss may become nearly zero, which can be very appropriate for the Time-Frequency analysis.

Figure 5A:
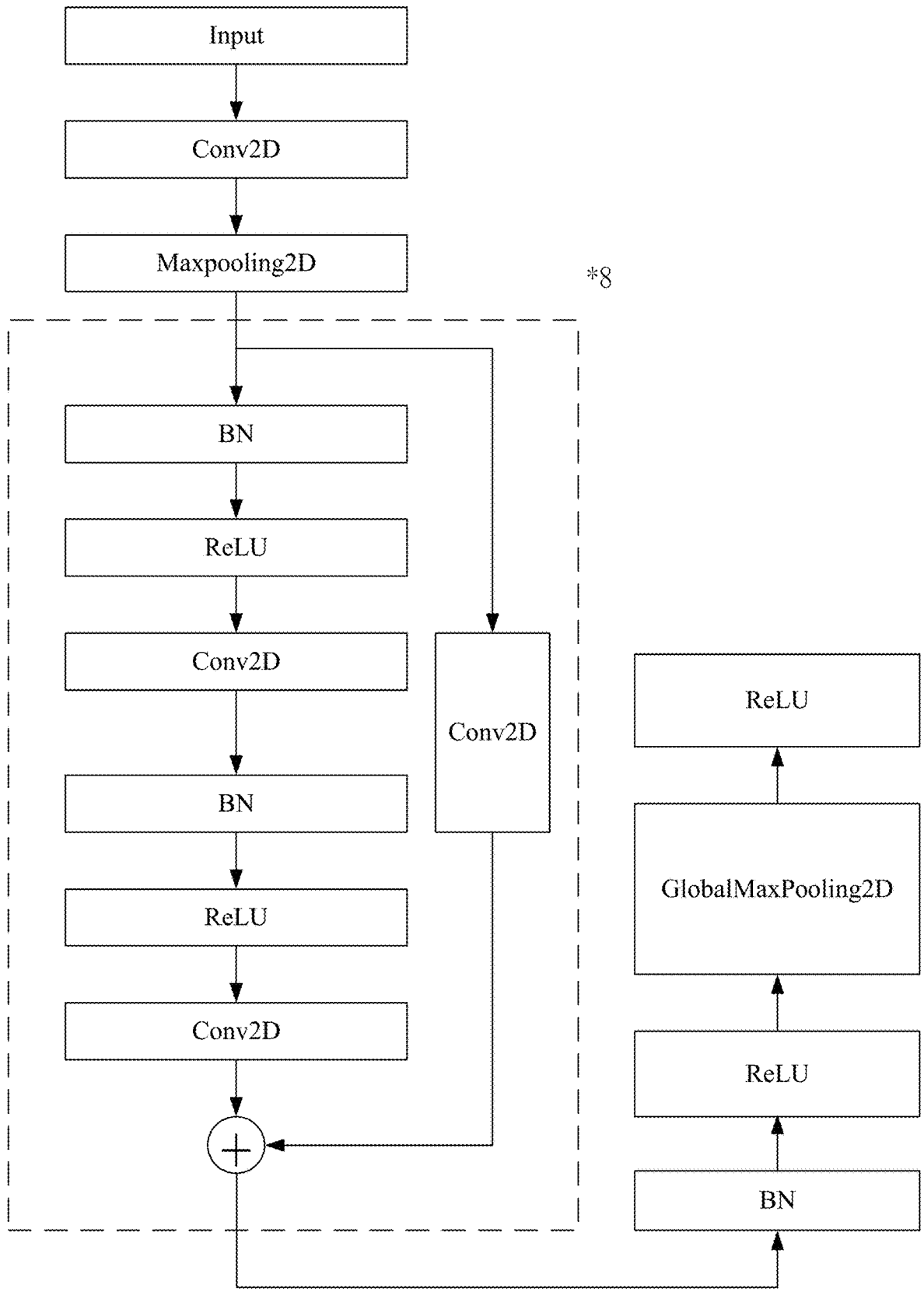
FIG. 5A shows a view of a conventional neural network model.

It can be seen from FIG. 5A that the present invention is based on the improvement on Res_block, which replaces the convolution part and the reduced space dimension part with the AvgPooling for training, and finally adding up a layer of GlobalAvgPooling2D and two layers of Dense for the final characteristics extraction. Besides, as shown in 5B, the reason of using AvgPooling is that the original architecture is applied in the image, while the "pixel and pixel" thereon has less relationship and the image itself is a quite complicated input; therefore, the present invention is designed to use Res_block so that it is possible to apply MaxPooling for dimension reductions which is a very reliable dimension reduction method, or alternatively to reserve the neighboring "pixel and pixel" relation by replacing the dimension reduction operation with the convolution operation, which also demonstrate quite good effect, so that both of the above-said approaches are capable of making the network converge faster. However, the reason that we chose AvgPooling is that, the image of our regression mission is the spectrogram, in which each time axis and next time axis in the spectrogram have relationship; hence, if MaxPooling is used, then many characteristics may be lost, so intuitively the convolution may be comparatively better. Therefore, we initially chose convolution to reduce the dimension, but later in the present invention the dimension reduction job is otherwise completed by means of AvgPooling, which provides a better performance than the originally applied convolution operation. As a result, all of the convolution dimension reductions jobs are totally replaced with the AvgPooling, which also demonstrates very good results in our database.

Figure 5B:
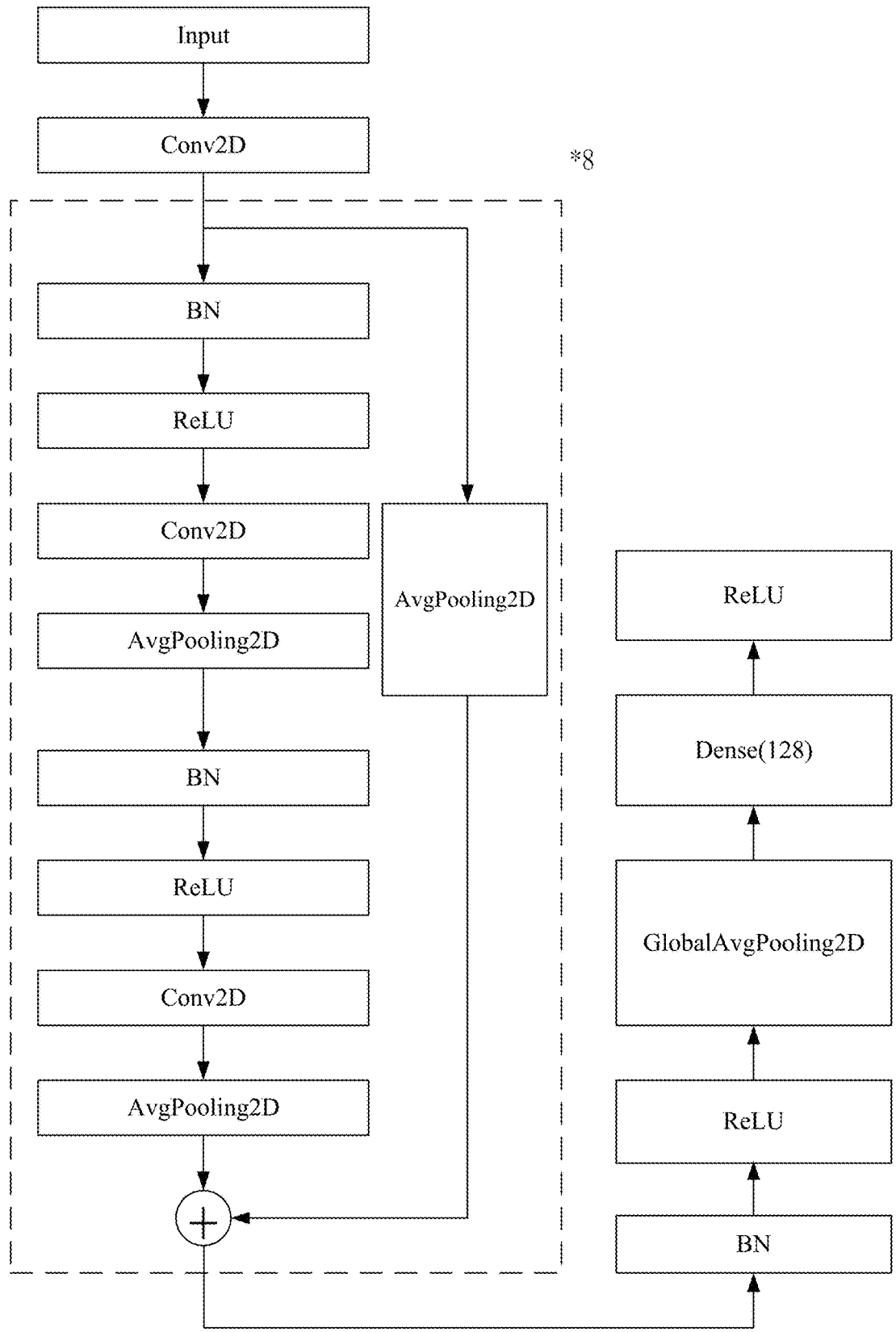
FIG. 5B shows a view for the improved neural network model in the heart rhythm detection method and system using radar sensor in accordance with the present invention.
Figures 1, 6A:
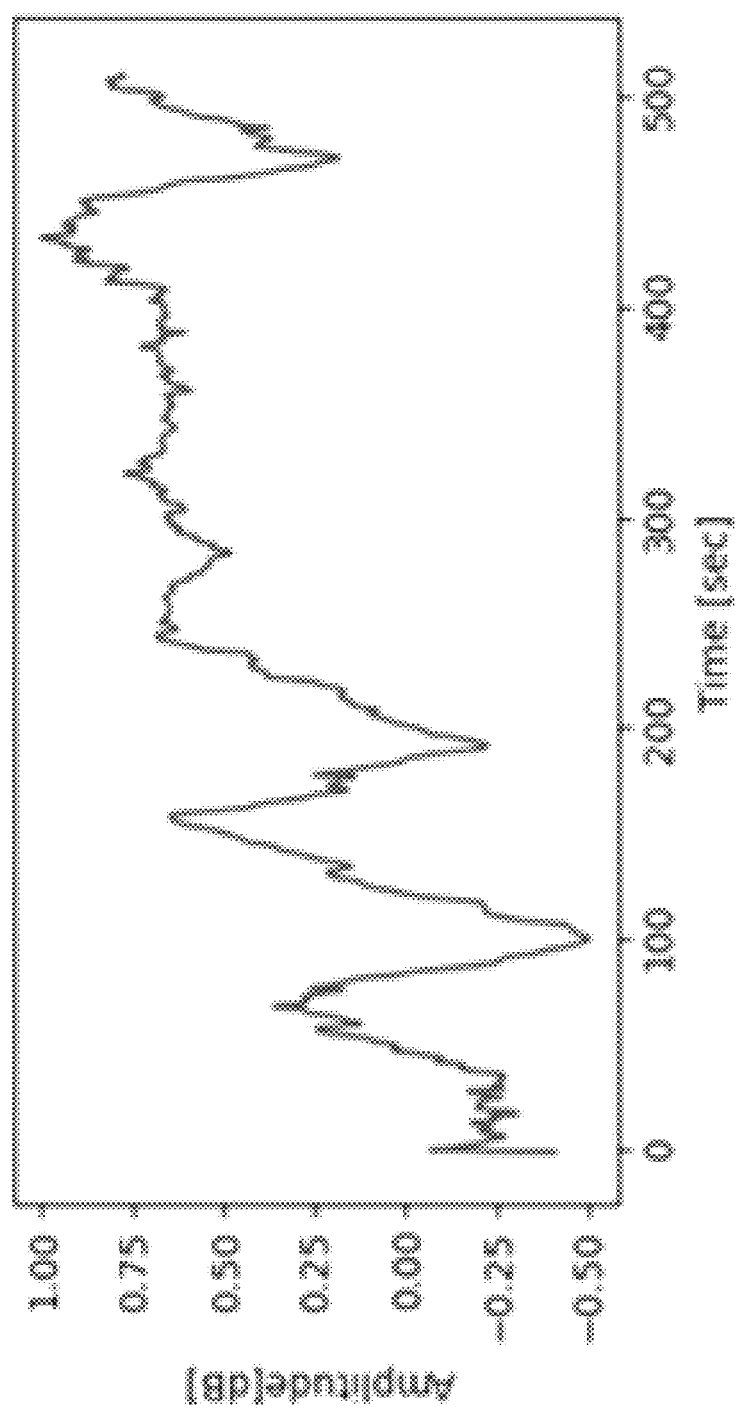
Figures 2, 6A:
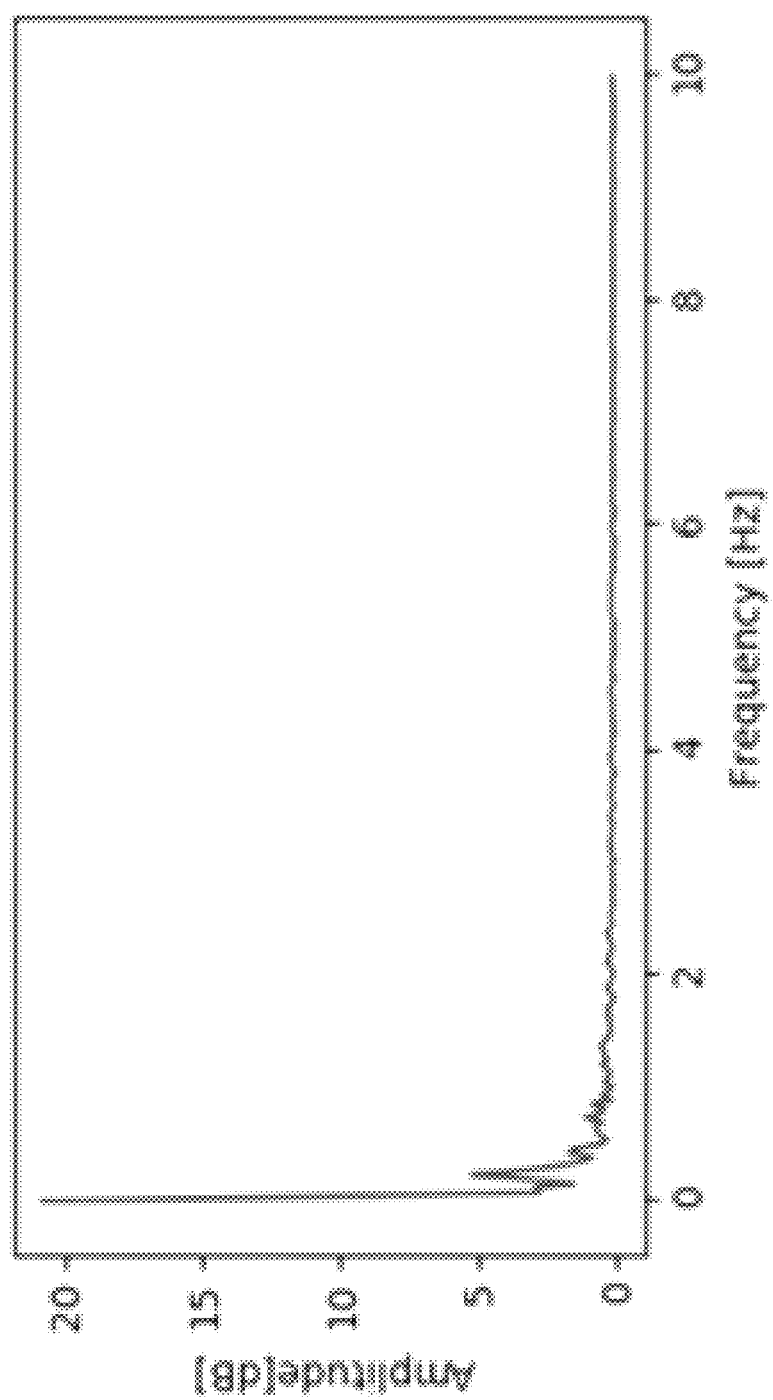
Figures 3, 6A:
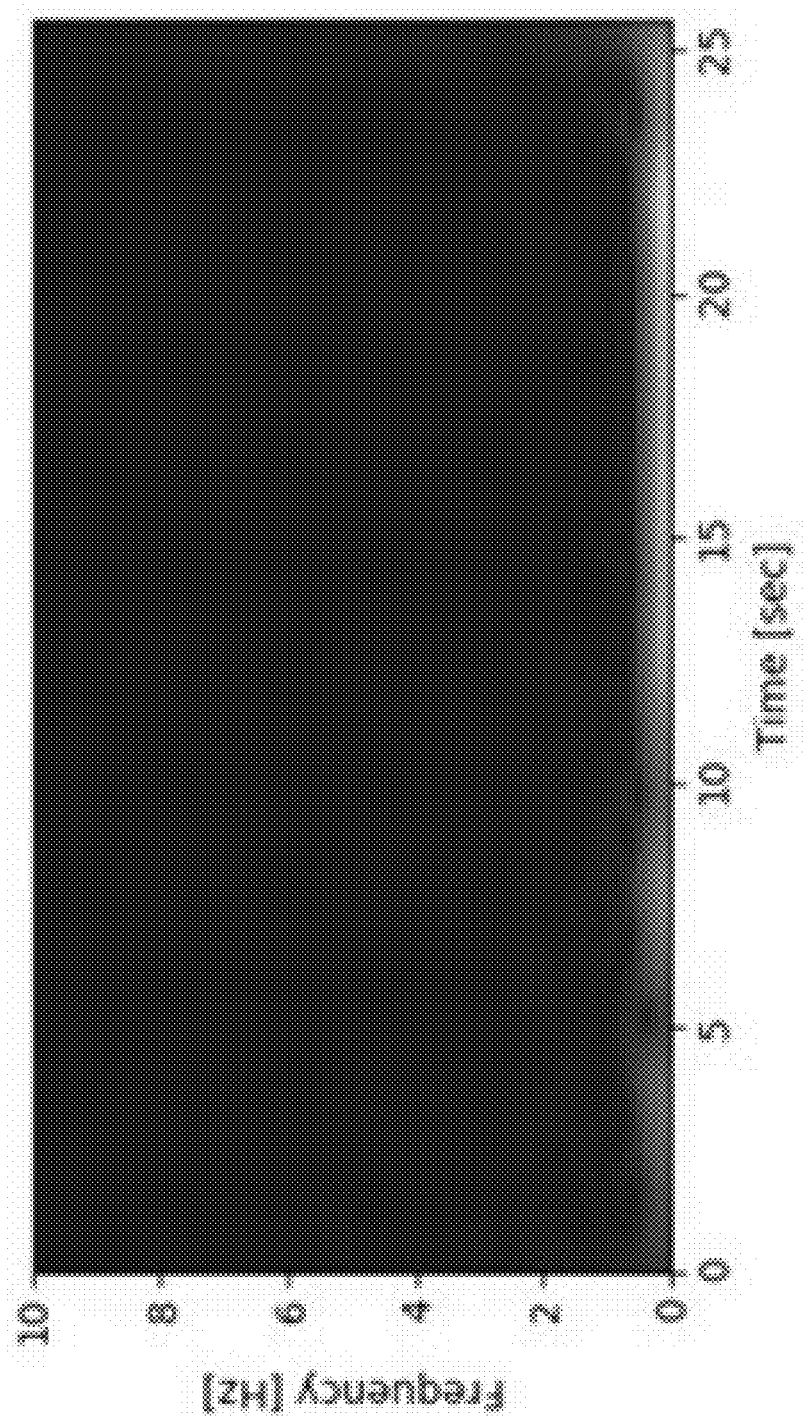
Figures 1, 6B:
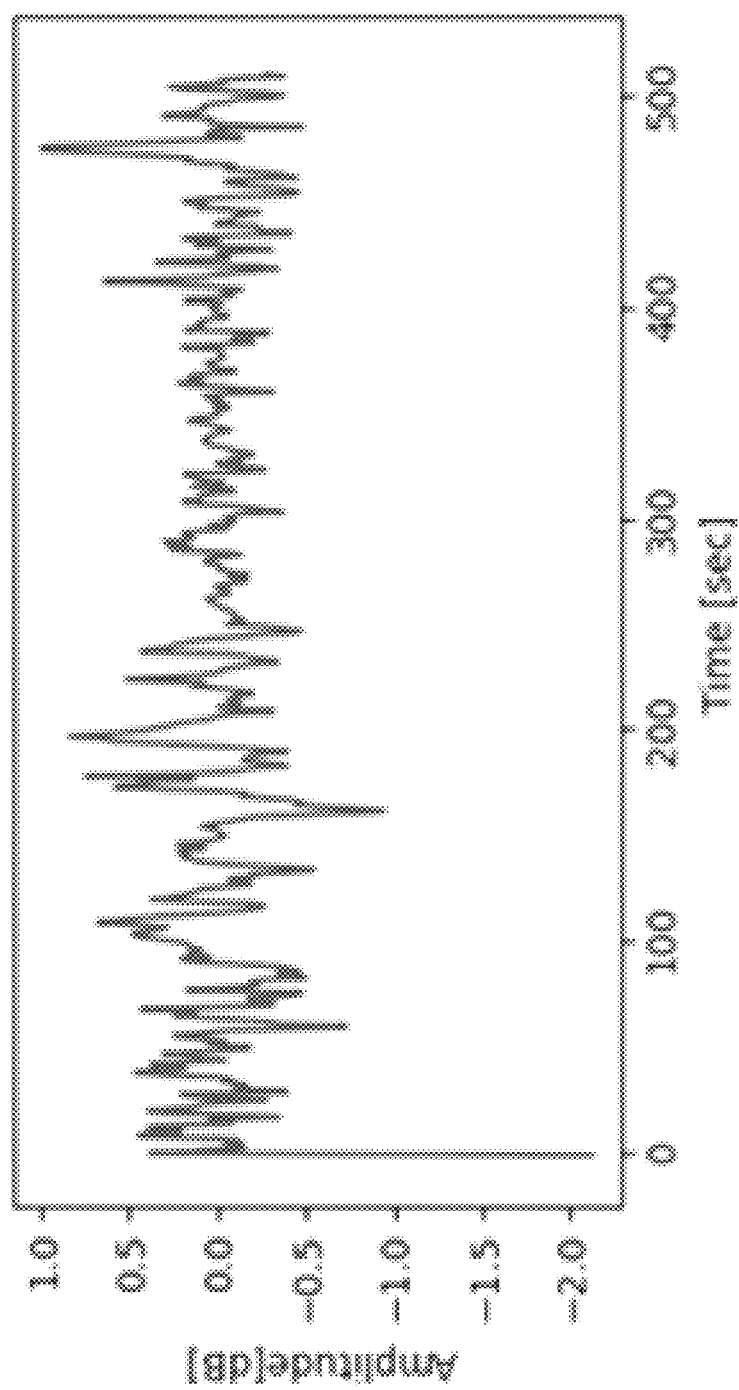
Figures 2, 6B:
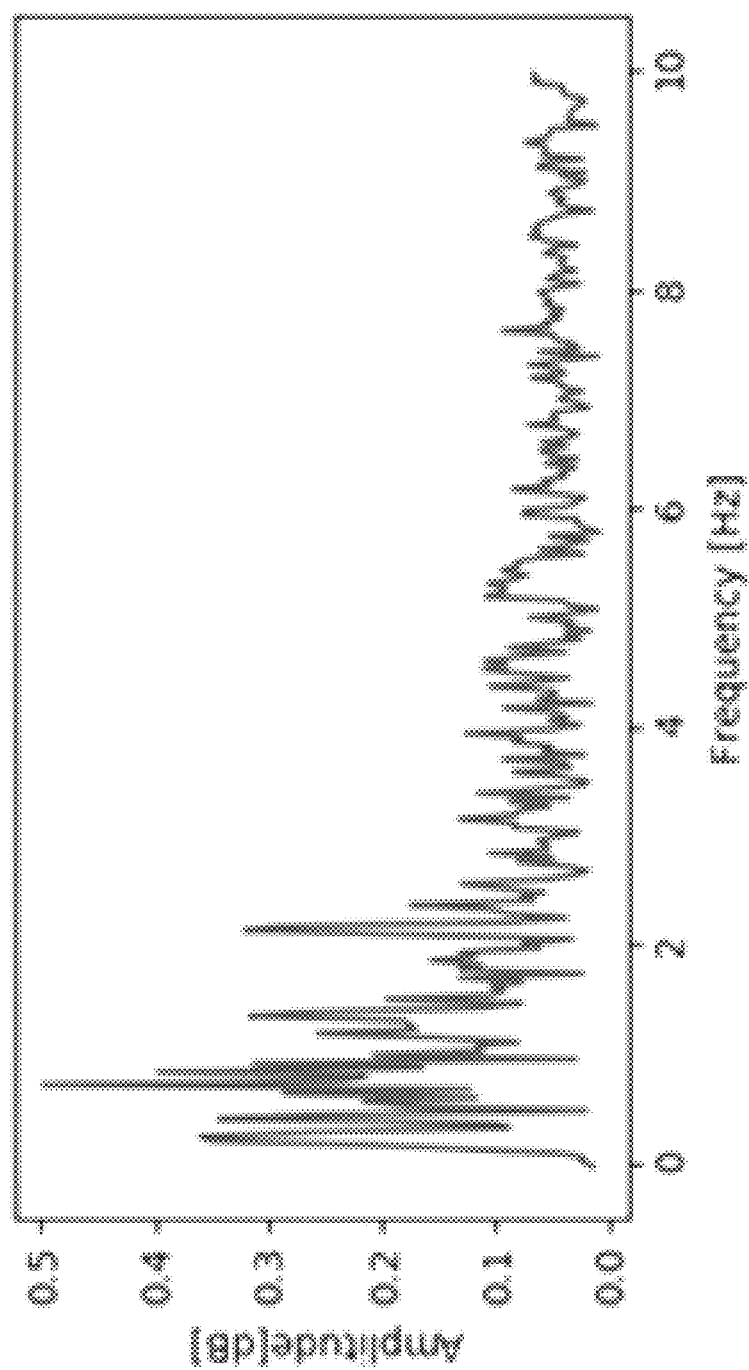
Figures 3, 6B:
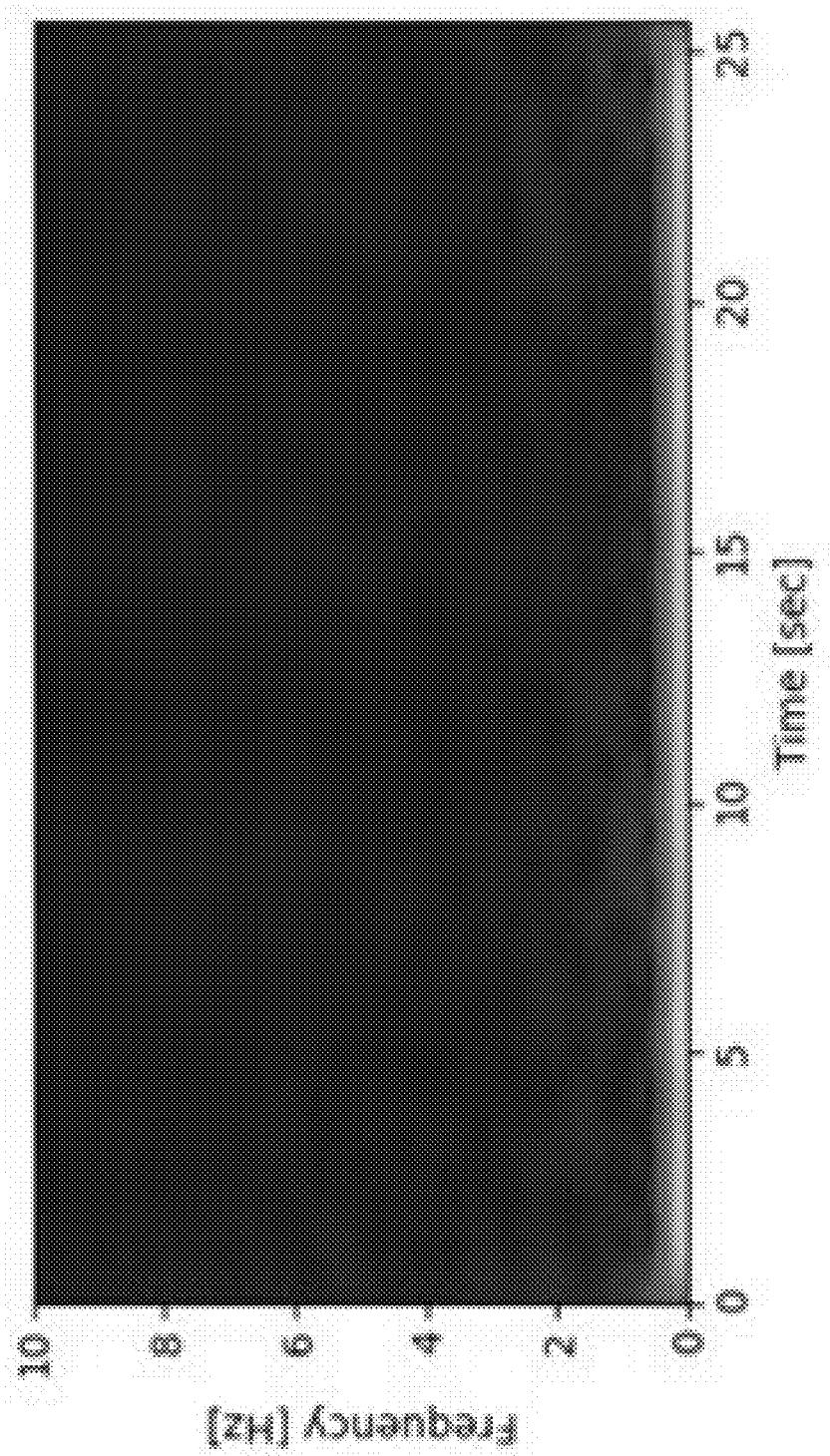
Figures 1, 6C:
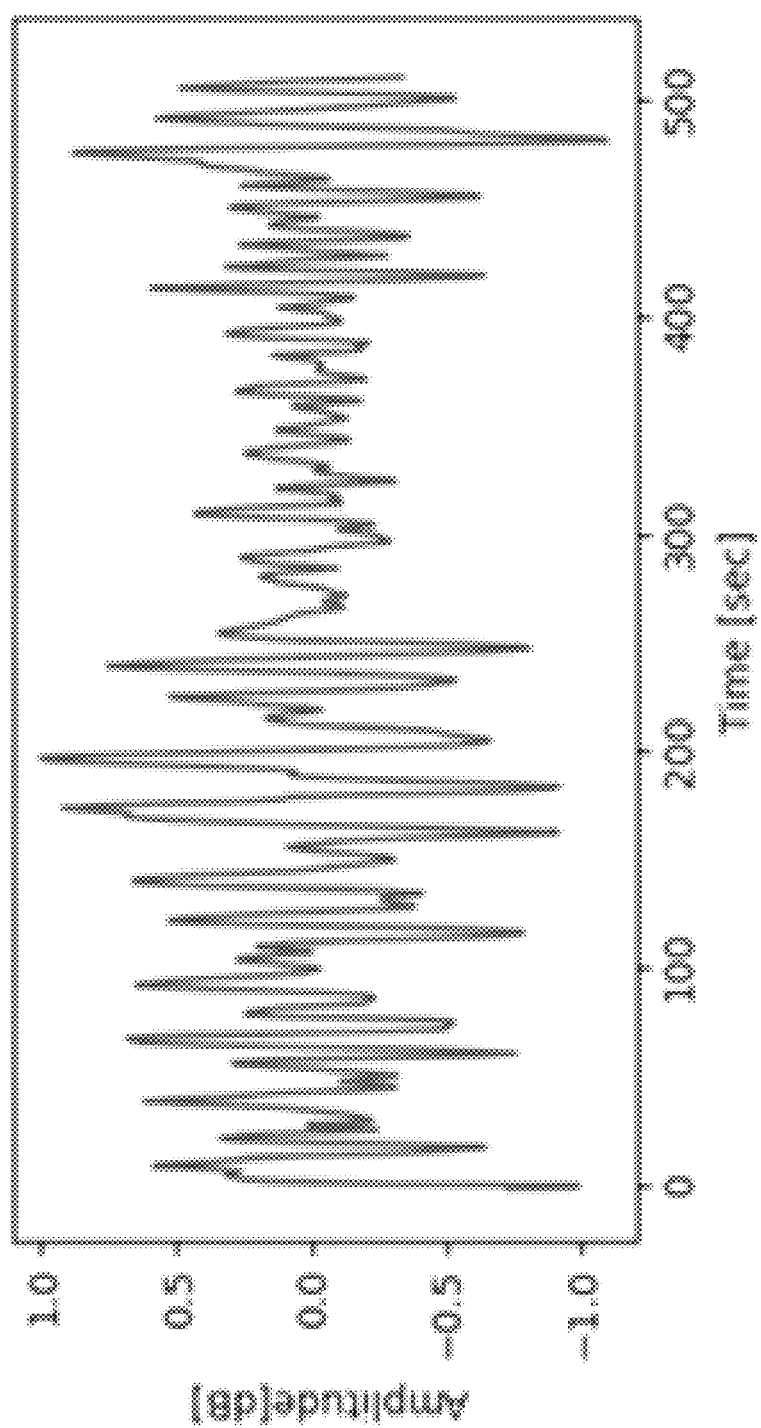
Figures 2, 6C:
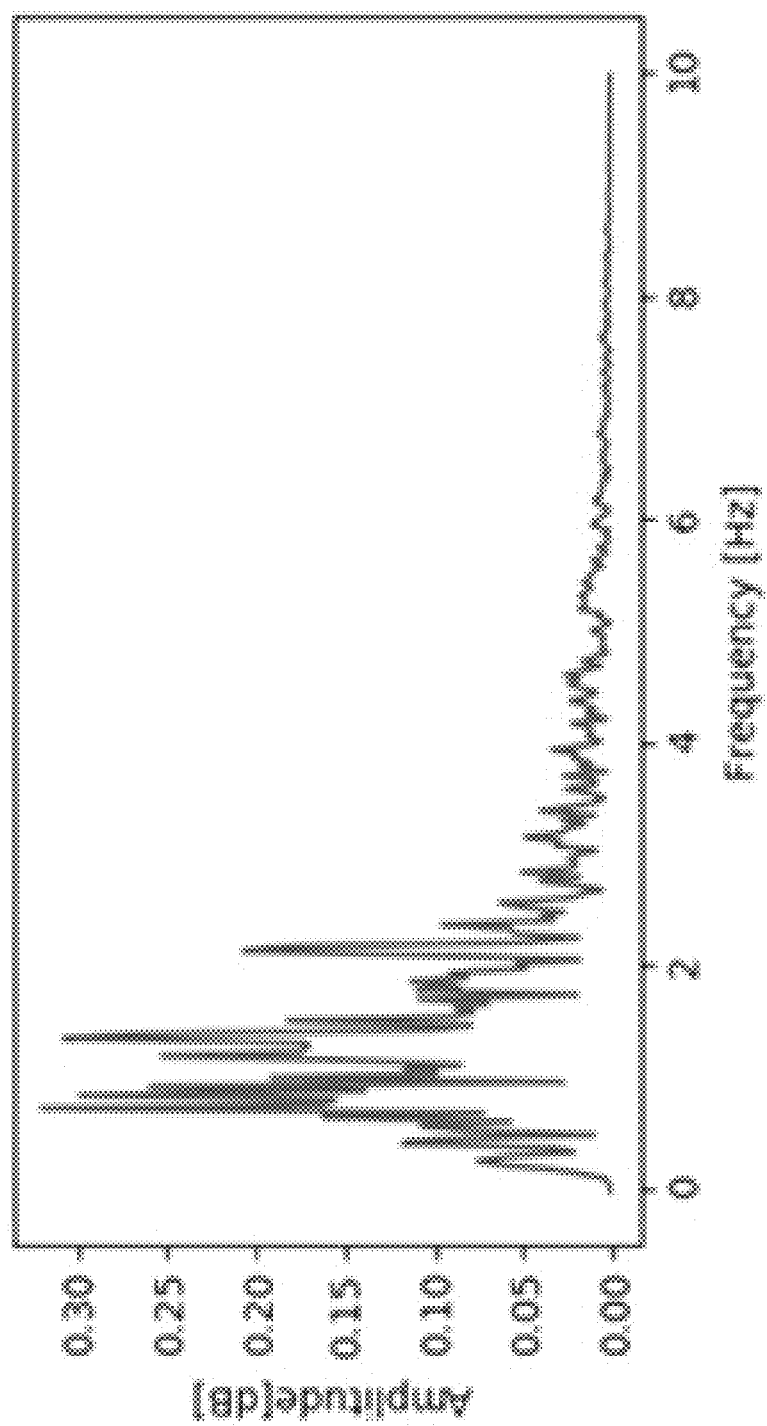
Figures 3, 6C:
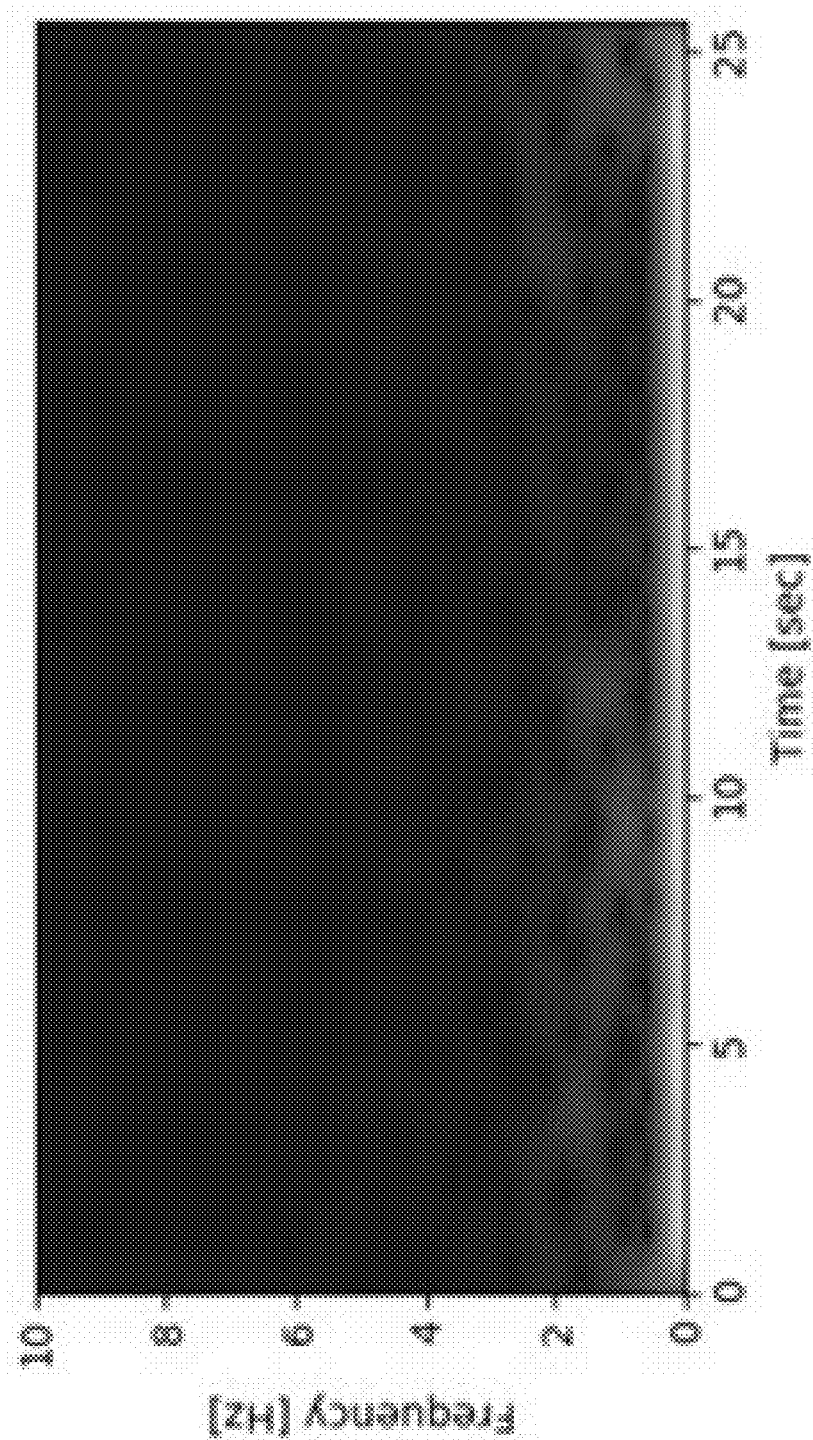

In FIG. 5B, "*8" represents the frame-sectioned range overlaps 8 times, while "+" symbol under the frame-sectioned range indicates adding up at that position.

The embodiment of the present invention adopts the frequency modulated continuous wave radar as the radar sensor 1, and the millimetre wave is applied for detecting the characteristics of small, weak signals to be recorded into our database; moreover, the present embodiment sets the erection height of the radar sensor 1 to a position of 1.8 meters above the heart, the received range signal is 20 cm, and the measurement angle is +/−20 degrees. Also, it is equipped with a pulse meter, and the measured pulse is used as the ground truth in the present embodiment.

In the present embodiment, it first isolates the position close to zero frequency by means of the high-pass filter, but reserves certain portions before 0.8 Hz, and then uses the band pass filter to keep the range 0.8~2.0 Hz and reserves some frequencies outside the masked range. The purpose of doing so is to allow the network to view more comprehensively, or otherwise some heart rhythms between 0.8~1 Hz or 1.8~2.0 Hz may undesirably lose the original frequency bands due to the filters. Finally, the filtered raw signal is conversed to the spectrogram by means of the STFT operation, as shown in FIGS. 6A-1, 6A-2, 6A-3, 6B-1, 6B-2, 6B-3, 6C-1, 6C-2 and 6C-3, in which the resulted diagrams indicating without filter, processed with the high-pass filter and processed with the band-pass filter, are respectively shown.

Next, when the input signal is pre-processed and converted to the spectrogram as previously described, it is then sent to the neural network for training. In the present embodiment, the Adam optimizer is used, and the initial learning rate is set to 10-3, the batch size is 25 and the total training epochs is 100, and according to the validation set loss function, an early stop with a patient of 10 is applied. Lastly, the loss function uses the Mean Absolute Error (MAE) to calculate the loss and call back the function.

Moreover, in the present embodiment, it should be seen that, in case of picking Res_Net18 to perform the 1D regression on the raw signal, the effect may be very poor and may not be easy to converge, or even using the band-pass filter may not improve such a difficulty in convergence, the true reason is that the raw signal is very complicated. So, in the present embodiment, after transforming the 1D raw signal to the spectrogram, the obtained 2D raw signal will be sent to Res_Net18 for training, whose outcome can also show a significant change indicating from the original over-fitting consequence to convergence.

The present invention adopts a loss function, MAE, which is capable of comparatively better representing the actual heart rhythm and the predicted heart rhythm, and through the MAE it is possible to calculate the errors with respect to the ground truth integrally in all tests; i.e., the lower the loss, the closer the overall result is to the true heart rhythm. In the present embodiment, the MAE loss function is used for verification, and suppose an appropriate filter is added in the pre-processing, it can also make the network have better convergence performance, thereby proving that the use of HPF and BPF for pre-processing can effectively let the neural network converge.

As shown in the following Table 1, it proves that, in the database recorded in the present embodiment (All_Data indicates all of the recorded data, while Avg_Data means the randomly selected data applied as the heart rhythm average database), in case that the original ResNet can be improved and all dimension reduction jobs are handled by means of the AvgPooling, it is possible to obtain better results, which also confirms that if it is applied to complicated missions and low sampling frequencies, such as radars, then, in order to allow the neural network to perform the Time-Frequency analysis, it is required to reserve more dependency information and also first set the neural network to particularly pay attention to certain areas; otherwise, probably due to excessive characteristics losses, the learning results may be finally just the same; in addition, after comparing the actual value with the predicted value, it can be seen that, by using the method offered in the present invention, the database proposed in the present embodiment can converge and the network can get closer and closer to the ground truth.

TABLE 1

The performance obtained by using different layers for dimension reduction, in which C is Conv2D and A is AvgPooling

| Database | Model | Signal Pre-Process | L1_loss |
|---|---|---|---|
| All_Data | ResNet18_CC | STFT | 8.0303 |
| | | HP + BP + STFT | 8.0410 |
| | ResNet18_CA | STFT | 8.1482 |
| | | HP + BP + STFT | 7.3049 |
| | ResNet18_AA | STFT | 8.1317 |
| | | HP + BP + STFT | 7.1721 |
| Avg_Data | ResNet18_CC | STFT | 9.7648 |
| | | HP + BP + STFT | 8.8205 |
| | ResNet18_CA | STFT | 9.8744 |
| | | HP + BP + STFT | 8.7038 |

TABLE 1-continued

The performance obtained by using different layers for dimension reduction, in which C is Conv2D and A is AvgPooling

| Database | Model | Signal Pre-Process | L1_loss |
|---|---|---|---|
| | ResNet18_AA | STFT | 9.7481 |
| | | HP + BP + STFT | 8.5715 |

It can be appreciated from the aforementioned embodiment that using high pass filter and band pass filter can reduce the influence of breathing signal on heartbeat signal, and at the same time make the neural network training demonstrate better performance; also, by applying the Short-Time Fourier Transform to convert the 1D signal to 2D signal, the issue concerning the difficulty of convergence for 1D ResNet can be resolved, and, additionally, by using the improved Res-Net for the characteristics extraction, thus allowing the AvgPooling to play the role of characteristics reservation in the spectrogram, it is possible to prevent the loss of any characteristics in the spectrogram upon ResNet training, thereby allowing the neural network to more precisely learn in the spectrogram and also more conveniently to converge.

Figure 7:
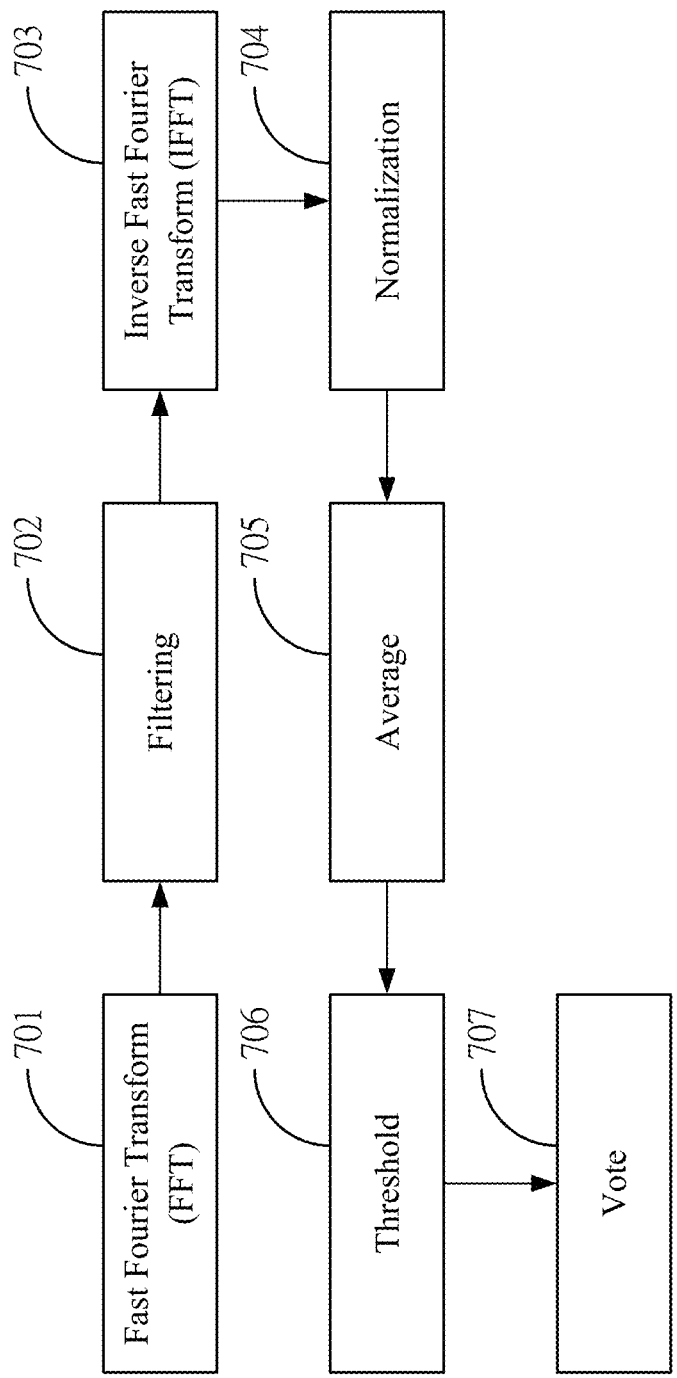
FIG. 7 shows a detection flowchart for the heart rhythm detection method and system using radar sensor in accordance with the present invention.

Furthermore, as shown in FIG. 7, it is required to first detect and determine whether the subject has left thereby maintaining the correctness of signal sampling, whose procedures are illustrated as below:
(1) Each group of the Overall Signal includes the signal of 6 seconds, and 20 sampling points are set for each second of the signal, so, after reading, there will be 120 sampling points (701), then using such inputted 120 sampling points to perform the Fast Fourier Transform (FFT) (702), thus obtaining the spectrum of the inputted signal of 6 seconds;
(2) The Step "FFT cut" is to reserve 0.2 Hz-3.4 Hz frequency and filter out the rest portions (703), whose purpose is to remove the significant noise signal found close to the 0 Hz in the original signal, so it is necessary to execute this step in order to filter out the signal we don't need;
(3) Afterwards, we perform the Inverse Fast Fourier Transform (IFFT) on the filtered spectrum so as to acquire the filtered signal (704), then execute the normalization process for subsequent calculations (705);
(4) Based on the normalized signal, calculating the average of such 6-second signal in order to determine whether it is within the regulated threshold value (706), and in case the average value does fall within the threshold value, we can recognize that the 6-second signal has the presence of human;
(5) The threshold value is set up in accordance with the computation on the database (707), and after figuring out the average value for each recorded data in the database, it learns to find out the maximum and the minimum to be applied as the threshold values of the current stage;
(6) however, using threshold values to determine whether it has the presence of human may cause a problem, that is, the determination may be erratic, and such a problem may be resolved by using a kind of voting mechanism (708).

Figure 8:
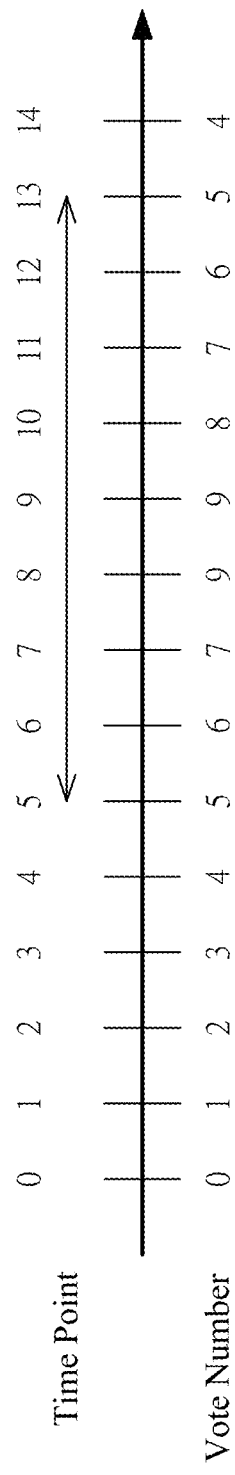
FIG. 8 shows a vote embodiment view for the heart rhythm detection method and system using radar sensor in accordance with the present invention.

Besides, as shown in FIG. 8, the number above is the time point and the number below is the vote number, with the initial value of the vote number being set to 0. Assume the time point for the presence of human is 0, so the vote number may add 1 at the time point 1, and since the person leaves at the time point 10, the vote number within such a duration of time will continuously add 1 until the maximum 9 then stop increasing 1. It should be noticed that, to determine whether the presence of human is true, it is required to reach 5 votes of the threshold value so as to make such a determination, so it can be understood that the presence of human will be determined only after the time point of 5. Subsequently, since the person leaves at the time point of 10, so the vote number will subtracts 1 at the time point 11 until the vote number reduces to the threshold value, then no presence of human will be recognized.

In comparison with other conventional technologies, the heart rhythm detection method and system using radar sensor according to the present invention provides the following advantages:

(1) The present invention provides a deep learning algorithm which adopts the Short-Time Fourier Transform (STFT) operation to convert the signal to two dimensional image information, applying the advantage of deep learning with respect to automatically finding the desired features, then using the network to find the relationship between the heartbeat frequency in the spectrogram and other non-heartbeat frequencies, and finally detecting the heart rhythm, which can solve the aforementioned uncertainty issues.

(2) The present invention applies the improved Res-Net for characteristics extractions in order to allow the AvgPooling to play the role of characteristics reservation in the spectrogram and prevent the loss of any characteristics in the spectrogram upon doing ResNet training, thereby allowing the neural network to more precisely learn in the spectrogram and also more conveniently to converge.

It should be noticed that, although the present invention has been disclosed through the detailed descriptions of the aforementioned embodiments, such illustrations are by no means used to restrict the scope of the present invention; that is, skilled ones in relevant fields of the present invention can certainly devise any applicable alterations and modifications after having comprehended the aforementioned technical characteristics and embodiments of the present invention without departing from the spirit and scope thereof. Hence, the scope of the present invention to be protected under patent laws should be delineated in accordance with the claims set forth hereunder in the present specification.

What is claimed is:

1. A heart rhythm detection method using radar sensor, comprising the following steps:

collecting a one dimensional raw signal by aligning at least one radar sensor toward at least one subject; and converting the one dimensional collected raw signal to two dimensional image information, then learning from the obtained two dimensional image information and automatically filtering out a noise signal by means of a neural network model so as to learn a relationship between a heartbeat frequency and non-heartbeat frequency of the two dimensional image information thereby extracting the heartbeat frequency;

wherein the one dimensional raw signal is first filtering processed then further converted to time-frequency dimension by means of a Short-Time Fourier Transform (STFT), thereby transforming the one dimensional raw signal to the two dimensional image information, and the two dimensional image information is a time-frequency view of a two dimensional image; and wherein the neural network model applies AvgPooling for training, and finally adding up a layer of GlobalAvgPooling2D and two layers of Dense for a final characteristic extraction.

2. The heart rhythm detection method using radar sensor according to claim 1, wherein the radar sensor is a one-millimeter wave radar.

3. The heart rhythm detection method using radar sensor according to claim 1, wherein the filtering process is applied to keep the one dimensional raw signal within the frequency domain of heart rhythm by means of the high-pass filtering and/or band-pass filtering process.

4. The heart rhythm detection method using radar sensor according to claim 1, further comprising first detecting and determining whether the subject is existed to maintain the correctness of signal sampling.

5. A heart rhythm detection system using radar sensor, comprising:

at least one radar sensor, used for collecting a one dimensional raw signal by aligning toward at least one subject; and at least one server equipment, used for connecting to the radar sensor and capable of receiving the one dimensional raw signal thus converting the collected one dimensional raw signal to two dimensional image information, then learning from the obtained two dimensional image information and automatically filtering out a noise signal by means of a neural network model so as to learn a relationship between a heartbeat frequency and non-heartbeat frequency of the two dimensional image information thereby automatically extracting the heartbeat frequency;

wherein the one dimensional raw signal is first filtering processed then further converted to time-frequency dimension by means of a Short-Time Fourier Transform (STFT), thereby transforming the one dimensional raw signal to the two dimensional image information, and the two dimensional image information is a time-frequency view of a two dimensional image; and wherein the neural network model applies AvgPooling for training and finally adding up a layer of GlobalAvgPooling2D and two layers of Dense for a final characteristic extraction.

6. The heart rhythm detection system using radar sensor according to claim 5, wherein the server equipment comprises at least one processor and at least one computer readable recording media, and the computer readable recording media stores at least one application program and further stores computer readable instructions such that, upon running the stored computer readable instructions by the processor, the application program can be executed thus converting a raw signal to two dimensional image information, then learning from the obtained two dimensional image information and automatically filtering out the noise signal by means of the neural network model so as to learn the relationship between the heartbeat frequency and non-heartbeat frequency of the two dimensional image information thereby automatically extracting the heartbeat frequency.

* * * * *